United States Patent
Majeed et al.

(10) Patent No.: US 10,894,029 B2
(45) Date of Patent: Jan. 19, 2021

(54) NEUROPROTECTIVE COMPOSITIONS AND THEIR USE

(71) Applicants: Muhammed Majeed, Edison, NJ (US); Kalyanam Nagabhushanam, East Windsor, NJ (US)

(72) Inventors: Muhammed Majeed, Edison, NJ (US); Kalyanam Nagabhushanam, East Windsor, NJ (US)

(73) Assignee: SAMI LABS LIMITED, Bangalore (IN)

( * ) Notice: Subject to any disclaimer, the term of this patent is extended or adjusted under 35 U.S.C. 154(b) by 0 days.

(21) Appl. No.: 16/009,490

(22) Filed: Jun. 15, 2018

(65) Prior Publication Data
US 2018/0360801 A1    Dec. 20, 2018

Related U.S. Application Data

(60) Provisional application No. 62/520,141, filed on Jun. 15, 2017.

(51) Int. Cl.
| | | |
|---|---|---|
| *A61K 31/352* | (2006.01) | |
| *A61P 27/06* | (2006.01) | |
| *A61P 25/28* | (2006.01) | |
| *A61P 25/16* | (2006.01) | |
| *A61P 39/00* | (2006.01) | |
| *A61K 31/353* | (2006.01) | |
| *A61K 9/00* | (2006.01) | |
| *A61K 36/185* | (2006.01) | |

(52) U.S. Cl.
CPC .......... *A61K 31/352* (2013.01); *A61K 31/353* (2013.01); *A61K 36/185* (2013.01); *A61P 25/16* (2018.01); *A61P 25/28* (2018.01); *A61P 27/06* (2018.01); *A61P 39/00* (2018.01); *A61K 9/0053* (2013.01)

(58) Field of Classification Search
CPC .. A61K 31/352; A61K 31/353; A61K 9/0053; A61P 39/00; A61P 27/06; A61P 25/28; A61P 25/16
See application file for complete search history.

(56) References Cited

U.S. PATENT DOCUMENTS

| | | | | |
|---|---|---|---|---|
| 2005/0096281 A1* | 5/2005 | Jia | ............... | A61K 31/35 514/27 |
| 2015/0231067 A1* | 8/2015 | Mann | ............... | A61K 9/0075 424/499 |

* cited by examiner

*Primary Examiner* — Sahar Javanmard

(57) ABSTRACT

Disclosed are compositions containing not less than 10% w/w of oroxylin A, not less than 10% w/w of baicalein and not less than 2% w/w of chrysin for use in the therapeutic management of memory impairment and cognitive dysfunction. More specifically, the invention discloses the use of abovementioned compositions for the management of cognitive impairment induced by chemotherapy and hyperglycemia.

12 Claims, 11 Drawing Sheets

NEUROPROTECTIVE COMPOSITIONS AND THEIR USE

CROSS-REFERENCE TO RELATED PATENT APPLICATION

The present invention is non-provisional filing of U.S. provisional patent application No. 62/520,141 filed on 15 Jun. 2017.

BACKGROUND OF THE INVENTION

Field of the Invention

The invention in general relates to compositions for neuroprotection. More specifically the present invention relates to therapeutic management of memory disorders and cognitive impairment using a composition containing oroxylin A, baicalein and chrysin.

Description of Prior Art

Dementia is a type of neurodegenerative disorder causing progressive decline in the mental and cognitive abilities. It is characterised by the presence of memory loss, cognitive impairment, disorientation, increasing difficulties with tasks and activities that require organisation and planning, mood changes, hallucinations and personality changes. There are different types of dementia which include Alzheimer's disease, Vascular dementia, Dementia associated with Parkinson's disease, Lewy body dementia, Fronto-temporal dementia, Creutzfeldt-Jakob disease, Wernicke's encephalopathy, Hydrocephalus, Huntington's disease, Vitamin B12 deficiency, thyroid dysfunction, anticholinergic medications, depression Sometimes, the disease may be present showing co-morbidity from one or more conditions from the abovementioned conditions. Generally, most types of dementia are irreversible and require regular medications to prevent further deterioration. Dementia that is associated with Vitamin B12 deficiency, thyroid dysfunction, medications and depression may be reversed with proper treatment and care.

The causes for the development of dementia and memory impairment are many fold, which include hyperglycemia, oxidative stress, inflammation, genetics, chemotherapy, medications, trauma, environmental pollutants, HIV infections, vascular complications etc. The following prior art documents describe the different types of dementia:

1. Corey-Bloom, et al., (1995). Diagnosis and evaluation of dementia. *Neurology*, 45(2), 211-218.
2. What is dementia?, Alzheimer's association, https://www.alz.org/what-is-dementia.asp, accessed on 10 Jun. 2018.
3. Nussbaum et al., (2003) Alzheimer's Disease and Parkinson's Disease, N Engl J Med; 48:1356-1364
4. Kim et al., (2013) Hyperglycemia-Induced Tau Cleavage in vitro and in vivo: A Possible Link Between Diabetes and Alzheimer's Disease, Journal of Alzheimer's Disease, 34(3): 727-739
5. Ahles et al. (2007) Candidate mechanisms for chemotherapy-induced cognitive changes, *Nature Reviews Cancer* volume 7, pages 192-201

There are many treatment strategies employed for the management and treatment of cognitive impairment and dementia. Owing to the multi-factorial nature of the condition, it is imperative that the causative factors for the development of cognitive disabilities and memory loss are identified and treatment is provided accordingly. Natural molecules that can confer neuroprotection against different types of dementia are now being increasingly evaluated. Some of the natural molecules that are reported to show neuroprotective effect are listed in the following prior art documents:

1. Mecocci et al., (2014) Nutraceuticals in cognitive impairment and Alzheimer's disease, Front Pharmacol. 2014; 5: 147.
2. Mendonça et al., (2013) Curcumin reduces cisplatin-induced neurotoxicity in NGF-differentiated PC 12 cells, NeuroToxicology, Volume 34, Pages 205-211.
3. Tiwari et al., (2018) Ethnopharmacological Approaches for Dementia Therapy and Significance of Natural Products and Herbal Drugs, Frontiers in Aging Neuroscience, 10, 1-24.
4. Dietary factors and dementia—Part 3: Plant derived substances that can make a difference. A weblog on the sciences and practices of living healthily very long—perhaps hundreds of years. Accessed from http://www.anti-agingfirewalls.com/2012/01/11/dietary-factors-and-dementia-%E2%80%93-part-3-plant-derived-substances-that-can-make-a-difference/on 22 Mar. 2018.
5. US20080096826, Formulation Of A Mixture Of Free-B-Ring Flavonoids And Flavans For Use In The Prevention And Treatment Of Cognitive Decline And Age-Related Memory Impairments.
6. Jeon et al., (2012) Oroxylin A Induces BDNF Expression on Cortical Neurons through Adenosine A2A Receptor Stimulation: A Possible Role in Neuroprotection. Biomol Ther 20(1), 27-35.

However, a natural molecule and/or a combination of natural molecules that confer neuroprotection, especially for chemotherapeutics-induced cognitive impairment and hyperglycemia induced cognitive impairment, are lacking. The present invention solves the above problem by disclosing a composition containing oroxylin A, baicalein and chrysin for management of memory loss and cognitive impairment associated with hyperglycemia and chemotherapy.

It is a principle objective of the invention to disclose a method for therapeutic management of chemotherapy induced cognitive impairment using a composition containing oroxylin A, baicalein and chrysin.

It is another objective of the invention to disclose a method for therapeutic management of hyperglycemia induced cognitive impairment using a composition containing oroxylin A, baicalein and chrysin.

It is yet another objective of the invention to disclose a composition containing oroxylin A, baicalein and chrysin, for use in the therapeutic management of memory impairment and cognitive dysfunction.

The invention fulfils the above mentioned objectives and provides further related advantages.

SUMMARY OF THE INVENTION

The present invention discloses a composition containing not less than 10% w/w of oroxylin A, not less than 10% w/w of baicalein and not less than 2% w/w of chrysin for use in the therapeutic management of memory impairment and cognitive dysfunction. More specifically, the invention discloses the use of the abovementioned composition in the management of cognitive impairment associated with chemotherapy and hyperglycemia.

DESCRIPTION OF THE MOST PREFERRED EMBODIMENTS

Figure 1:
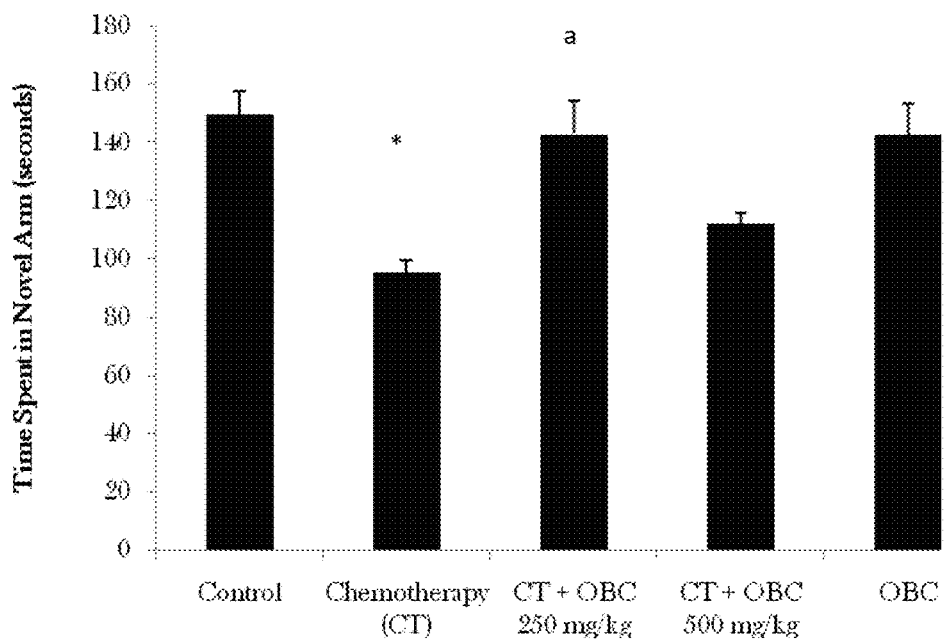
FIG. 1 is a graphical representation of the Y maze test showing increase in the time spent in the novel arm by chemotherapy treated animals administered with a composition containing oroxylin A, baicalein and chrysin.

In the most preferred embodiment the invention discloses a method of therapeutic management of chemotherapeutics-induced neurotoxicity in mammals, said method comprising steps of administering effective concentration of a composition containing not less than 10% w/w of oroxylin A, not less than 10% w/w of baicalein and not less than 2% w/w of chrysin, to mammals in need of such therapeutic management. In a related embodiment, the composition preferably comprises 10%-15% w/w of oroxylin A, 10%-25% w/w of baicalein and 2%-10% w/w of chrysin. In another related embodiment, the composition confers neuroprotection by improving cognition, decreasing oxidative stress, and enhancing mitochondrial function in the brain of mammals. In another related embodiment, improvement in cognition is brought about by improving response time, orientation, recognition, short term working memory, spatial navigation and recall. In a related embodiment, decrease in oxidative stress in brought about by decreasing the levels of reactive oxygen species (ROS), decreasing lipid peroxidation and increasing the glutathione content in the brain of mammals. In another related embodiment, enhancement in mitochondrial function is brought about by increasing activity of complex I and complex IV in the mammalian brain. In a preferred embodiment, the mammal is human. In another preferred embodiment, the composition is formulated with pharmaceutically/nutraceutically acceptable excipients, adjuvants, diluents or carriers and administered orally in the form of tablets, capsules, syrups, gummies, powders, suspensions, emulsions, chewables, candies and eatables.

In another preferred embodiment the invention discloses a method of therapeutic management of hyperglycemia induced neurotoxicity in mammals, said method comprising steps of administering effective concentration of a composition containing not less than 10% w/w of oroxylin A, not less than 10% w/w of baicalein and not less than 2% w/w of chrysin, to mammals in need of such therapeutic management. In a related embodiment, the composition preferably comprises 10%-15% w/w of oroxylin A, 10%-25% w/w of baicalein and 2%-10% w/w of chrysin. In another related embodiment, the composition confers neuroprotection by decreasing oxidative stress and enhancing mitochondrial function in the brain of mammals, thereby improving cognition. In a related embodiment, decrease in oxidative stress in brought about by decreasing the levels of reactive oxygen species (ROS), decreasing lipid peroxidation and nitrate content in the brain of mammals. In another related embodiment, enhancement in mitochondrial function is brought about by increasing activity of complex I and complex IV in the mammalian brain. In a related embodiment, hyperglycemia is a pathological feature of diseases selected from, but not limited to, diabetes, hypercholesterolemia, Alzheimer's disease, mild cognitive impairment, pancreatitis, carcinoma, and hyperthyroidisim. In a preferred embodiment, the mammal is human. In another preferred embodiment, the composition is formulated with pharmaceutically/nutraceutically acceptable excipients, adjuvants, diluents or carriers and administered orally in the form of tablets, capsules, syrups, gummies, powders, suspensions, emulsions, chewables, candies and eatables.

In another preferred embodiment, the invention discloses a composition containing not less than 10% w/w of oroxylin A, not less than 10% w/w of baicalein and not less than 2% w/w of chrysin, for use in the therapeutic management of memory impairment and cognitive dysfunction. In a related embodiment, the composition preferably comprises 10%-15% w/w of oroxylin A, 10%-25% w/w of baicalein and 2%-10% w/w of chrysin. In another related embodiment, memory impairment and cognitive dysfunction are present in the disorders selected from the group consisting of Alzheimer's disease. Vascular dementia. Parkinson's disease, Lewy body dementia, Fronto-temporal dementia, Creutzfeldt-Jakob disease, Wemicke's encephalopathy, Hydrocephalus, Huntington's disease, Vitamin B12 deficiency, thyroid dysfunction, anticholinergic medications induced dementia, chemotherapy induced cognitive dysfunction, hyperglycemia, and depression. In another preferred embodiment, the composition is formulated with pharmaceutically/nutraceutically acceptable excipients, adjuvants, diluents or carriers and administered orally in the form of tablets, capsules, syrups, gummnies, powders, suspensions, emulsions, chewables, candies and eatables.

The specific examples included herein below illustrate the aforesaid most preferred embodiments of the present invention.

Example 1: Effects of Composition Containing Oroxylin A, Baicalein and Chrysin (OBC) on Chemotherapy Induced Memory Impairment The composition containing oroxylin A, baicalein and chrysin (OBC), was isolated from *Oroxylum indicum* as per the process mentioned in U.S. Ser. No. 15/805,320.

Methodology: The neuroprotective effects of the composition containing oroxylin A, baicalein and chrysin (OBC) in the chemotherapeutic-induced toxicity was evaluated. Mice received intraperitoneal (ip) injection of saline or chemotherapeutics (doxorubicin-2 mg/kg & cyclophosphamide-50 mg/kg) one injection/week for 4 weeks. The composition containing oroxylin A, baicalein and chrysin (250 and 500 mg/kg) was mixed with powdered rodent food and fed daily for 4 weeks. The neuroprotective effects was assessed by analyzing the effects on cognition and biochemical parameters in the brain.

Effects on Cognition

For studying the effect on cognition, three behavioral tests were performed, Y-maze test, Morris Water maze test. Novel Object Recognition test and open filed orientation.

Y-Maze Test

The Y-maze test is an index of spatial working memory. The test is based on the ability of the mice to explore a novel arm when presented compared to previously explore arms. The percentage entry into the novel vs previously explored arms (% novel arm entry), and spontaneous alternation scores for each mouse were calculated. These calculations reflect short-term working memory and spatial navigation, respectively (Ahuja et al., (2017) Immunological alteration & toxic molecular inductions leading to cognitive impairment & neurotoxicity in transgenic mouse model of Alzheimer's disease, Life Sciences 177 (2017) 49-59).

The results indicated that chemotherapeutics significantly decreased the time spent in the novel arm of the Y-maze as compared to the control (n=10, *$p<0.05$). Mice treated with a composition containing oroxylin A, baicalein and chrysin significantly spent more time in the novel arm compared to the chemotherapeutic treated mice (n=10, $^a p<0.05$) (FIG. 1), indicated an improvement in the short-term working memory and spatial navigation.

Morris Water Maze Test

Figure 2:
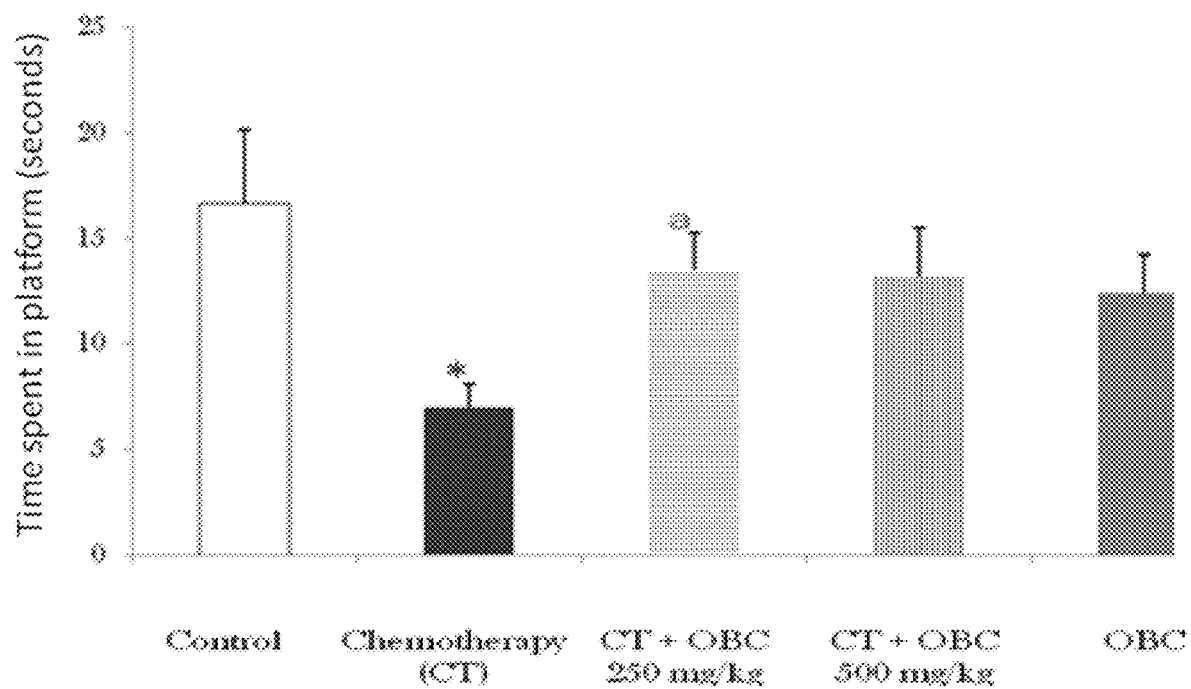
FIG. 2 is a graphical representation of the Morris water maze test showing increase in the time spent in the platform quadrant by chemotherapy treated animals administered with a composition containing oroxylin A, baicalein and chrysin.

The Morris water maze test was performed as per the protocol mentioned by Nunez et al., (2008). Morris Water Maze Experiment, J Vis Exp 19: 897. The Morris water maze is widely used to study spatial memory and learning. Chemotherapeutics significantly decreased the time spent in platform Quadrant as compared to the control (n=10, *$p<0.05$). The composition containing oroxylin A, baicalein and chrysin (250 mg/kg) significantly increased the time spent in the platform Quadrant in the chemotherapeutic treated mice (n=10, $^a p<0.05$, as compared to the Chemotherapeutics) (FIG. 2). This indicates that the composition significantly improves the learning ability and spatial memory which were absent in the chemotherapy treated mice.

Novel Object Recognition Test

Figure 3:
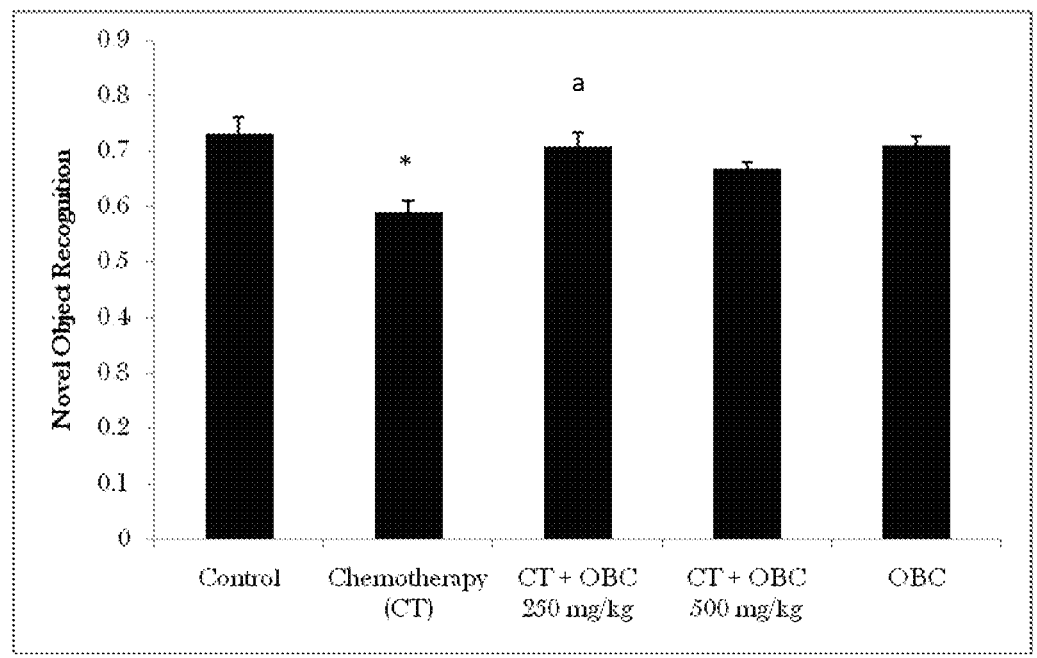
FIG. 3 is a graphical representation of the novel object recognition test showing increase in recognition index by chemotherapy treated animals administered with a composition containing oroxylin A, baicalein and chrysin.

The Novel Object Recognition task is very useful tool to evaluate short-term memory, intermediate-term memory, and long-term memory in animal models, through manipulation of the retention interval. The amount of time the animals retain memory of the sample objects presented during the familiarization phase before to the test phase, when one of the familiar objects is replaced by a novel one was evaluated. The test was performed as per the protocol described by Ahuja et al., (2017) Immunological alteration & toxic molecular inductions leading to cognitive impairment & neurotoxicity in transgenic mouse model of Alzheimer's disease, Life Sciences 177 (2017) 49-59. The results indicated that Chemotherapeutics significantly decreased the number of touched on the novel object as compared to the control (n=10, *$p<0.05$). Mice treated with the composition significantly increased the number of touches on the novel object when co-administered with chemotherapeutics (n=10, $^a p<0.05$, as compared to the Chemotherapeutics) (FIG. 3).

Open Field Test

Figure 4:
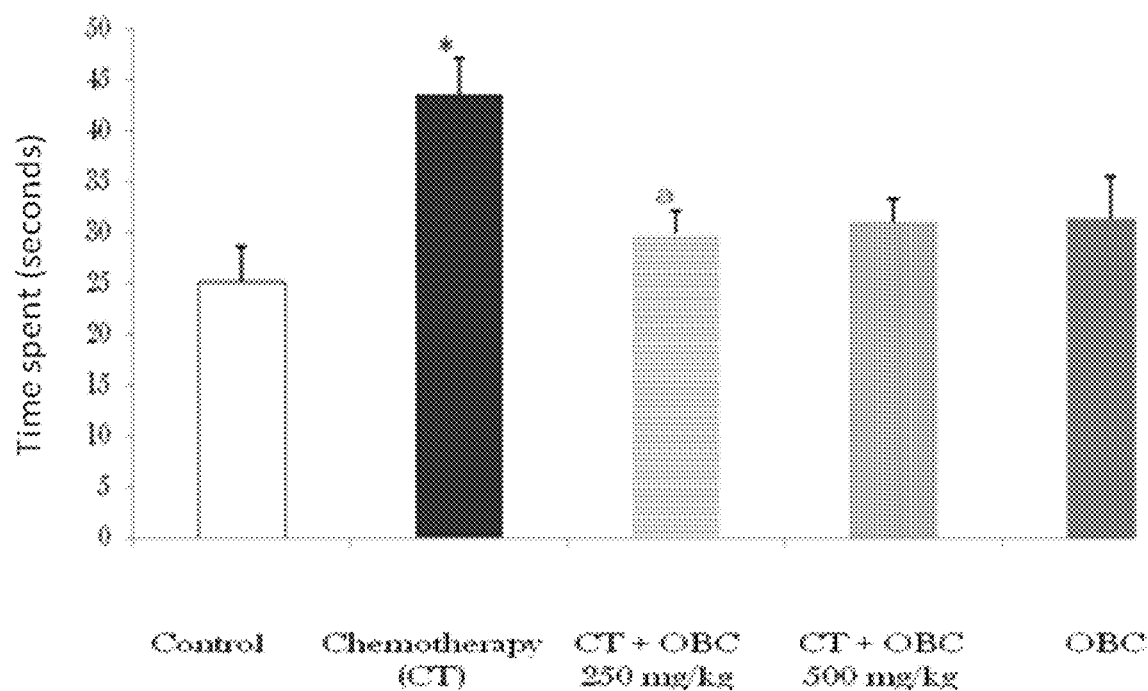
FIG. 4 is a graphical representation of the open field orientation test showing increase in the time spent in the centre by chemotherapy treated animals administered with a composition containing oroxylin A, baicalein and chrysin.

The open field test is a widely used model of anxiety-like behaviour developed to evaluate emotionality in animals and is based on subjecting an animal to an unknown environment whose escape is prevented by surrounding walls. The test was performed as per the protocol described by Ahuja et al., (2017) Immunological alteration & toxic molecular inductions leading to cognitive impairment & neurotoxicity in transgenic mouse model of Alzheimer's disease, Life Sciences 177 (2017) 49-59. Chemotherapeutics significantly increased the amount of time spent in the center as compared to the control (n=10, *$p<0.05$). The composition significantly reduced the amount of time spent in the center as compared to the chemotherapeutics (n=10, $^a p<0.05$, as compared to the Chemotherapeutics) (FIG. 4)

The Y-maze, Novel Object Recognition and Open Field procedure were used to evaluate the neuroprotective effects of the composition on cognition. One benefit of the above tests are that the cognitive demands of the task can be increased or decreased by varying the number of daily training trials and time from training until probe trial (e.g., 24 vs. 72 hours). Primary dependent measures include (a) swim speed, (b) path length to find hidden platform (during training), and (c) platform crossing index and percent time in target quadrant (during probe testing). To ensure any deficits observed in the water maze are not due to visual or motor deficits, the visible platform test will be performed as previously described at the end of water maze testing. Chemotherapeutic treatment significantly induced cognitive impairment. The composition containing oroxylin A, baicalein and chrysin significantly protected against the cognitive impairment induced by chemotherapeutics.

Biochemical Parameters

The biochemical parameters for neuroprotection, like total ROS, lipid peroxidation and glutathione content were estimated in brain of the animal as per the procedure described in by Ahuja et al., (2017) Immunological alteration & toxic molecular inductions leading to cognitive impairment & neurotoxicity in transgenic mouse model of Alzheimer's disease, Life Sciences 177 (2017) 49-59.

Figure 5A:
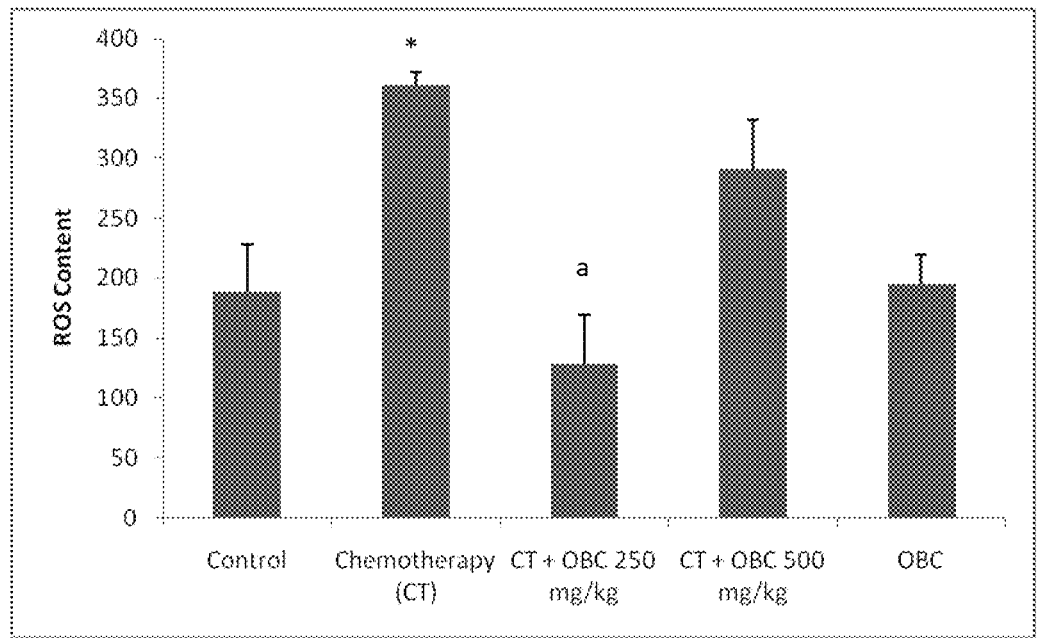
FIG. 5a is a graphical representation of the reduction in ROS levels in the cortex of chemotherapy treated animals administered with a composition containing oroxylin A, baicalein and chrysin.
Figure 5B:
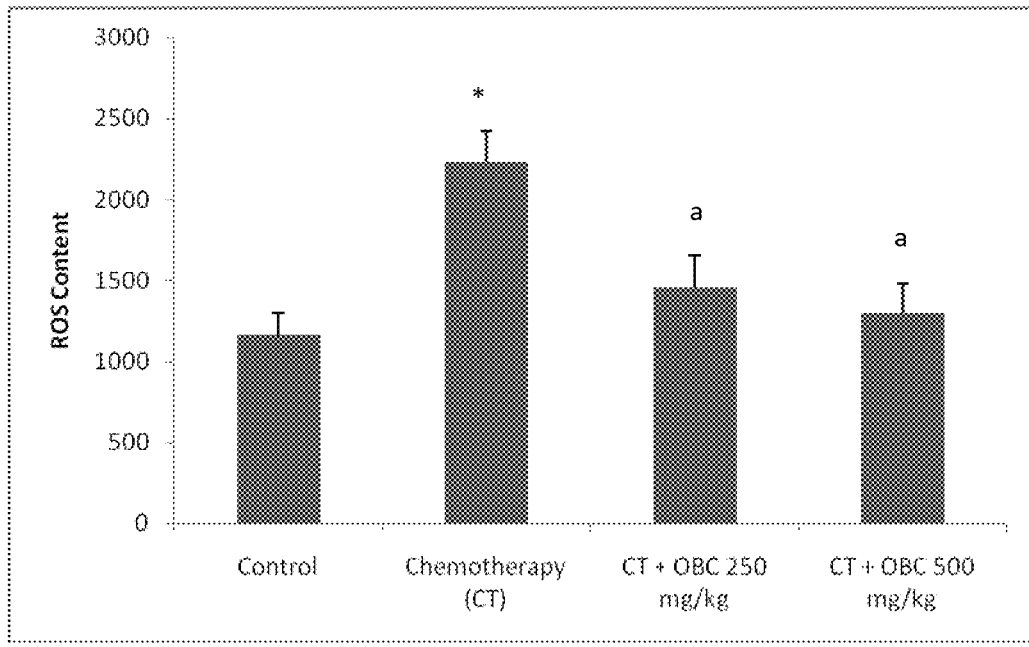
FIG. 5b is a graphical representation of the reduction in ROS levels in brain (other than cortex) of chemotherapy treated animals administered with a composition containing oroxylin A, baicalein and chrysin.

Chemotherapeutics (CT) significantly increased the generation of ROS in the cortex and rest of the brain as compared to the control (n=5, $*p<0.05$). The composition containing oroxylin A, baicalein and chrysin (250 mg/kg) significantly lowered the ROS generated by CT in the cortex (FIG. 5a). However, the composition at 250 mg/kg and 500 mg/kg body weight significantly lowered the ROS generated by CT in the rest of the brain (n=5, $^a p<0.05$) (FIG. 5b).

Figure 6A:
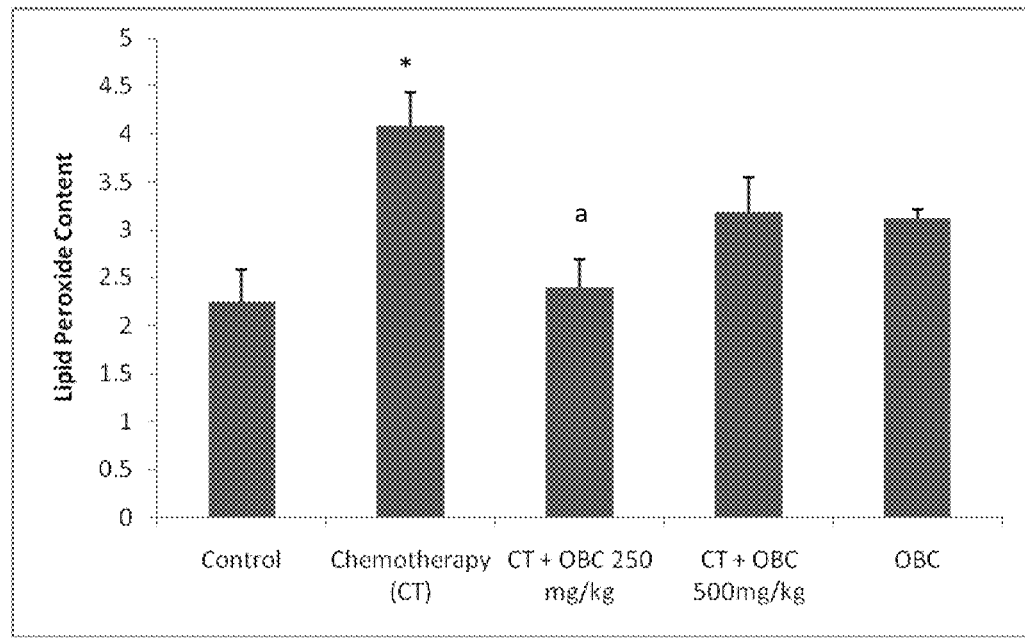
FIG. 6a is a graphical representation of the reduction in lipid peroxidation in the cortex of chemotherapy treated animals administered with a composition containing oroxylin A, baicalein and chrysin.
Figure 6B:
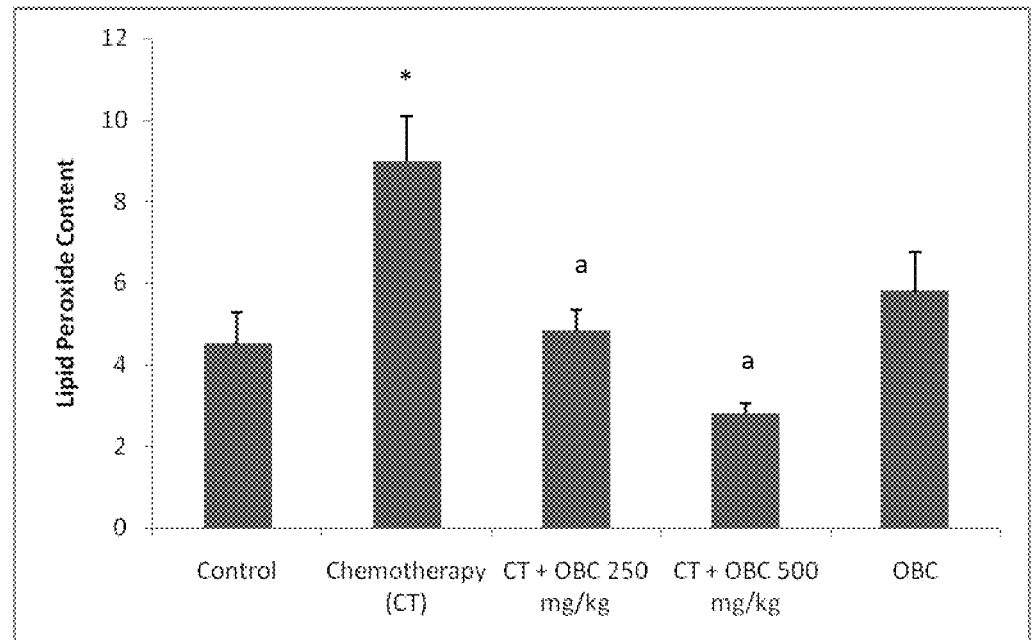
FIG. 6b is a graphical representation of the reduction in lipid peroxidation in brain (other than cortex) of chemotherapy treated animals administered with a composition containing oroxylin A, baicalein and chrysin.
Figure 7A:
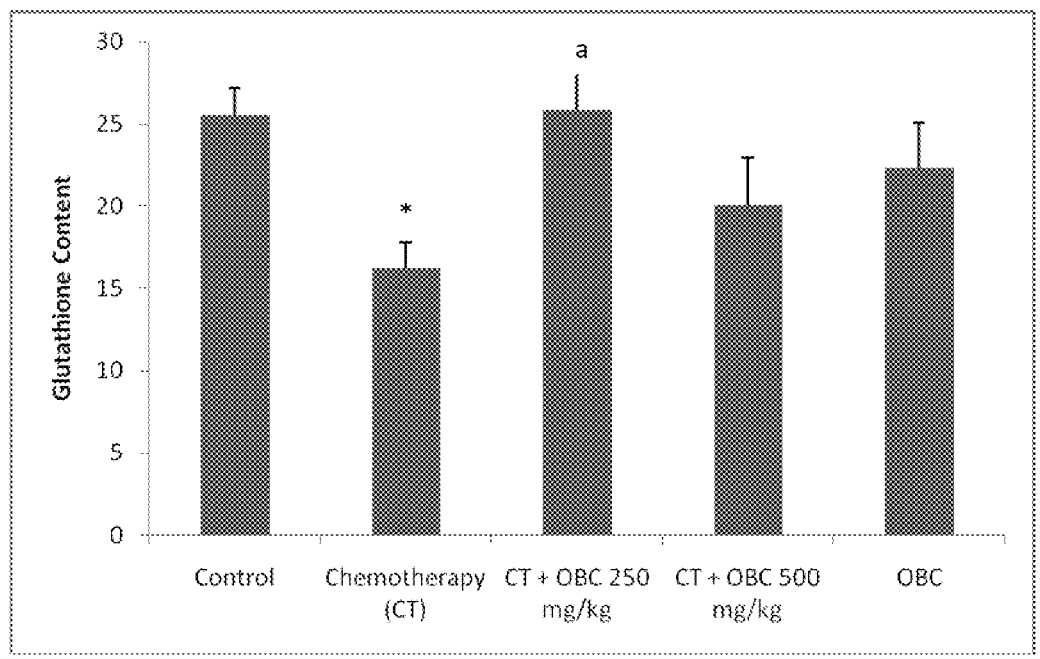
FIG. 7a is a graphical representation of the increase in glutathione content in the cortex of chemotherapy treated animals administered with a composition containing oroxylin A, baicalein and chrysin.
Figure 7B:
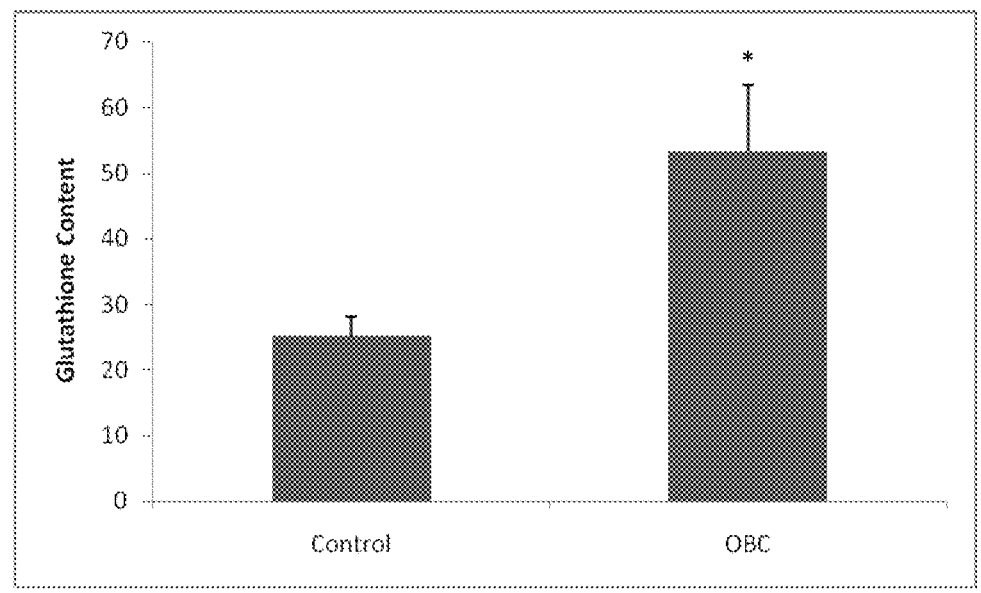
FIG. 7b is a graphical representation of the increase in glutathione content in brain (other than cortex) of chemotherapy treated animals administered with a composition containing oroxylin A, baicalein and chrysin.

The lipid peroxidation was significantly elevated in the cortex of the mice undergoing chemotherapy as compared to the control (n=5, $*p<0.05$). The composition at 250 mg/kg body weight significantly lowered the lipid peroxide generated by CT in the cortex (FIG. 6a) and in the rest of the brain, both the concentrations of the composition decreased lipid peroxidation (FIG. 6b) (n=5, $^a p<0.05$). Chemotherapy significantly depleted the glutathione content in the cortex as compared to the control in the cortex (n=5, $*p<0.05$). The composition at 250 mg/kg significantly blocked the CT-induced glutathione depletion in the cortex (FIG. 7a)(n=5, $^a p<0.05$). The composition alone significantly increased the glutathione content in the rest of the brain (n=5, $^a p<0.05$) (FIG. 7b).

Enhancement of Mitochondrial Function

The role of mitochondria in memory impairment is well established. Reports indicated the decrease in activity of complex I and complex IV with aging (Swerdlow (2011) Brain aging, Alzheimer's disease, and mitochondria, Biochim Biophys Acta. 2011 December; 1812(12): 1630-1639). The activity of the complexes were also reported to be impaired in Alzheimer's induced memory dysfunction (Rhein et al., (2009) Amyloid-β and tau synergistically impair the oxidative phosphorylation system in triple transgenic Alzheimer's disease mice, Proc Natl Acad Sci USA 2009 Nov. 24; 106(47): 20057-20062). Hence, enhancement of the mitochondrial complex can be an important target in alleviating the symptoms of memory impairment.

Figure 8A:
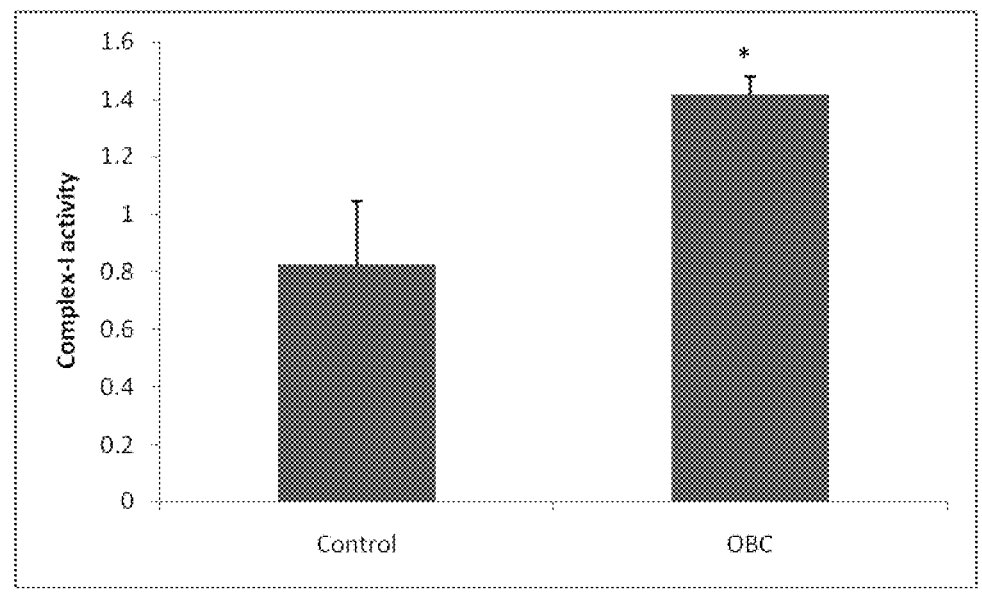
FIG. 8a is a graphical representation of the increase in complex I in the cortex of chemotherapy treated animals administered with a composition containing oroxylin A, baicalein and chrysin.
Figure 8B:
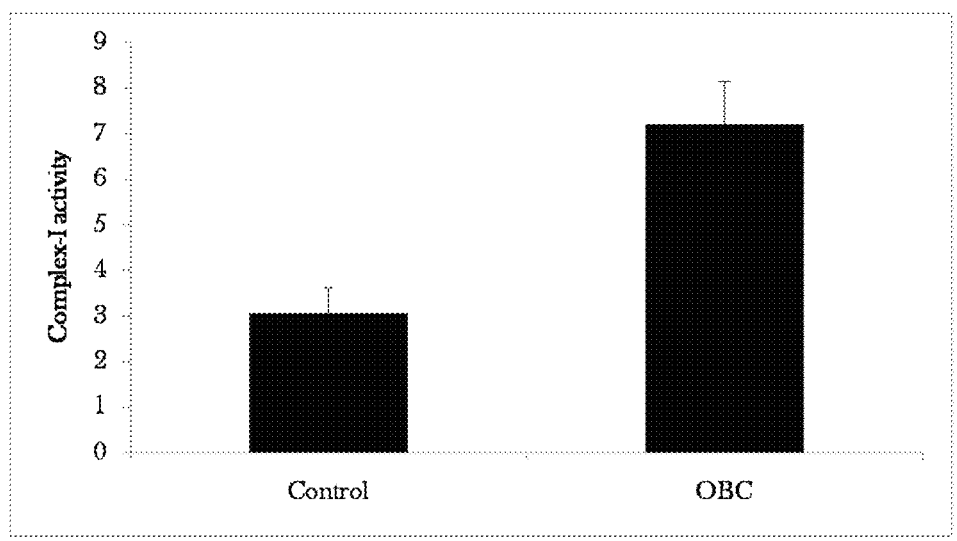
FIG. 8b is a graphical representation of the increase in complex I in brain (other than cortex) of chemotherapy treated animals administered with a composition containing oroxylin A, baicalein and chrysin.
Figure 9A:
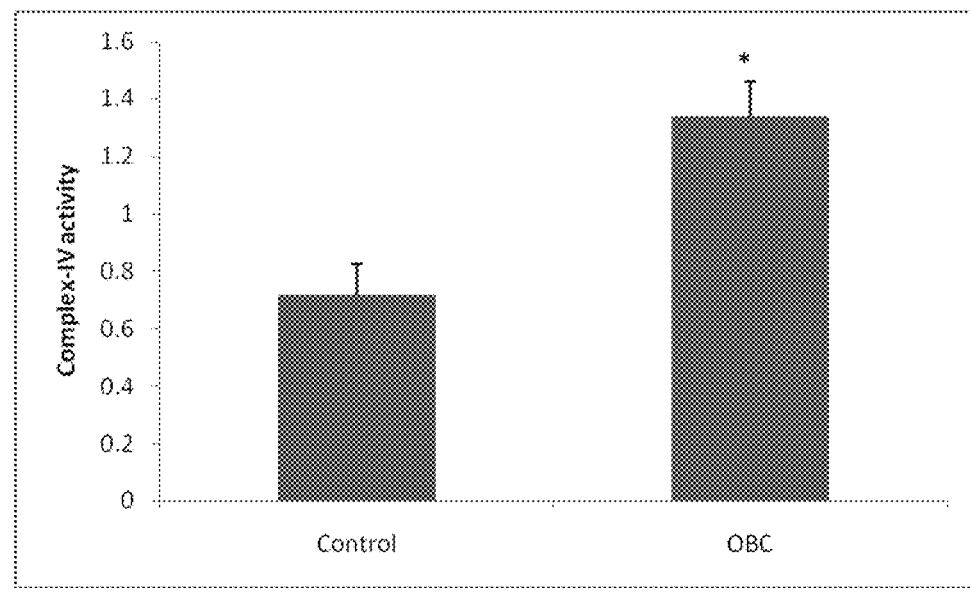
FIG. 9a is a graphical representation of the increase in complex IV in the cortex of chemotherapy treated animals administered with a composition containing oroxylin A, baicalein and chrysin.
Figure 9B:
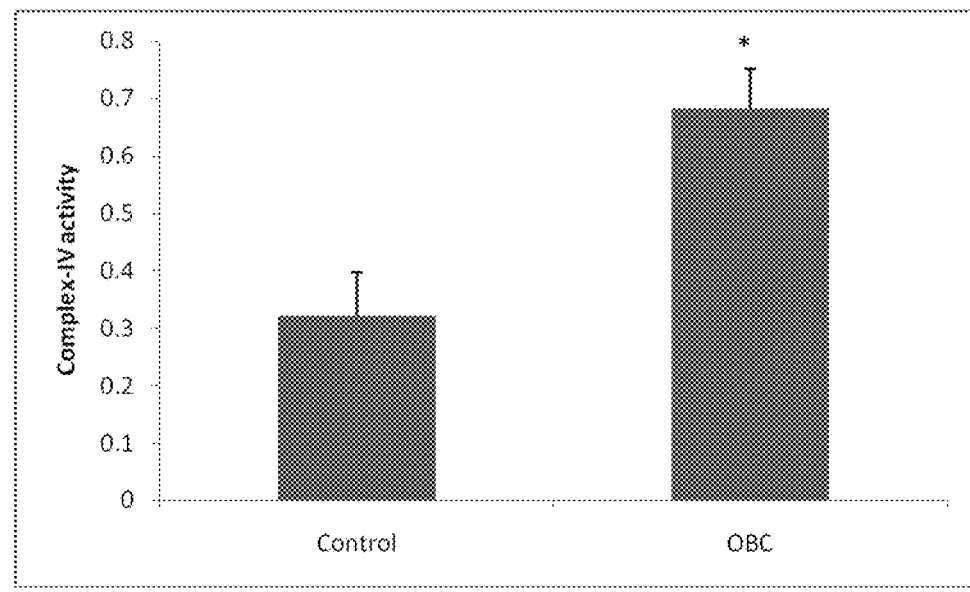
FIG. 9b is a graphical representation of the increase in complex IV in brain (other than cortex) of chemotherapy treated animals administered with a composition containing oroxylin A, baicalein and chrysin.

In the present study, the composition containing oroxylin A, baicalein and chrysin significantly increased the activity of complex I in both the cortex (FIG. 8a) and in the rest of the brain (FIG. 8b). Similarly, complex IV was also enhanced in the cortex (FIG. 9a) and in the rest of the brain (FIG. 9b) by the composition, compared to the control.

General Behavioral Markers:

The control and composition (500 mg/kg) treated mice were monitored regularly for several behavioral parameters. Based on effect of body weight and monitoring of the general behavior, the composition containing oroxylin A, baicalein and chrysin (OBC) did not show any major toxicity. Furthermore, the composition also had no significant adverse effects pertaining to the Central Nervous System (CNS), Gastrointestinal system (GIT) and Genitourinary system.

The results are tabulated in Table 1.

TABLE 1

Behavioral parameters

| Behavioral Parameters | Control | OBC (500 mg/kg) |
|---|---|---|
| Abnormal posture (head press) | N | N |
| Aggressive behavior (fight) | N | N |
| Agitation | N | N |
| Allergic reaction (redness of the skin or eye) | N | N |
| Anaphylactic shock/death | N | N |
| Body weight (% increase in 5 weeks) | 17% | 6.7% |
| Bowel movement | N | N |
| Diarrhea | None | None |
| Drooling | N | N |
| Emesis | None | None |
| Eye bulging | N | N |
| Fighting (Aggressive behavior) | N | N |
| Grinding teeth/Chattering | N | N |
| Grooming | Y | Y |
| Hair coat erection | N | N |
| Head twitching | N | N |
| Hematuria | N | N |
| Hind limb abduction | N | N |
| Hyperactivity (excessive jumping) | N | N |
| Licking body | N | N |
| Licking genitals | N | N |
| Mortality observed | N | N |
| Locomotion (increase/decrease) | N | N |
| Narcolepsy | N | N |
| Open mouth breathing | N | N |
| Penile erection (stimulatory behavior) | N | N |
| Rapid Breathing | N | N |
| Salivation/Drool | N | N |
| Seizure | N | N |
| Sniffing | N | N |
| Stool color | N | N |
| Straub tail | N | N |
| Sunken eyes/lack of blinking | N | N |
| Tremor | N | N |
| Tumor | N | N |
| Wiggling Whiskers | N | N |

Y = yes, N = no

Conclusion

Overall, the composition containing oroxylin A, baicalein and chrysin improved congnition, reduced oxidative stress and increased mitochondrial functions in the brain. The composition showed significant neuroprotective effects and can be used to reduce neurodegeneration in neurodegenerative disorders such as Alzheimer's and Parkinson's disease. It not only counteracted the chemotherapy effects but also enhanced the beneficial biochemical aspects on its own and conferred neuroprotection.

Example 2: Effects of Composition Containing Oroxylin A, Baicalein and Chrysin (OBC) on Hyperglycemia Induced Memory Impairment The composition containing oroxylin A, baicalein and chrysin (OBC), was isolated from *Oroxylum indicum* as per the process mentioned in U.S. Ser. No. 15/805,320.

Methodology: The neuroprotective effects of the composition containing oroxylin A, baicalein and chrysin (OBC) in the hyperglycemia associated toxicity was evaluated. Rats received intraperitoneal (ip) injection of saline or streptozotocin (STZ) (55 mg/kg). The composition containing oroxylin A, baicalein and chrysin (OBC) (250 and 500 mg/kg) was mixed with powdered rodent food and fed daily for 4 weeks. The neuroprotective effects was assessed by analyzing the effects on cognition and biochemical parameters in the brain.

Effects on Cognition

For studying the effect on cognition, three behavioral tests were performed, Y-maze test, Morris Water maze test, Novel Object Recognition test and open filed orientation. The tests were performed using the procedures as described example I.

We assessed the spatial learning and memory using the Morris water maze, Y-maze, and Object recognition. One benefit of the above testsare that the cognitive demands of the task can be increased or decreased by varying the number of daily training trials and time from training until probe trial (e.g., 24 vs. 72 hours). Primary dependent measures include (a) swim speed. (b) path length to find hidden platform (during training), and (c) platform crossing index and percent time in target quadrant (during probe testing). To ensure any deficits observed in the Morris water maze are not due to visual or motor deficits, the visible platform test will be performed as previously described at the end of Morris water maze testing. The Y-maze, the object recognition test were used to evaluate the neuroprotective effects of the composition containing oroxylin A, baicalein and chrysin on cognition.

With regard to Y-maze and Water maze, the composition did not alone did not affect the alternations in the novel arm, dwell time and latency to novel arm as compared to the control. Thus, the composition alone had no toxic effect on cognition. Streptozotocin significantly induced cognitive impairment, but since the animals were very hyperglycemic, the treatment could not counteract the neurotoxicity induced by streptozotocin. With regard to the Morris Water Maze also the effects were similar to the Y-maze.

Biochemical Parameters

The biochemical parameters for neuroprotection, like total ROS, lipid peroxidation and glutathione content were estimated in brain of the animal as per the procedure described in by Ahuja et al., (2017) Immunological alteration & toxic molecular inductions leading to cognitive impairment & neurotoxicity in transgenic mouse model of Alzheimer's disease, Life Sciences 177 (2017) 49-59.

Figure 10:
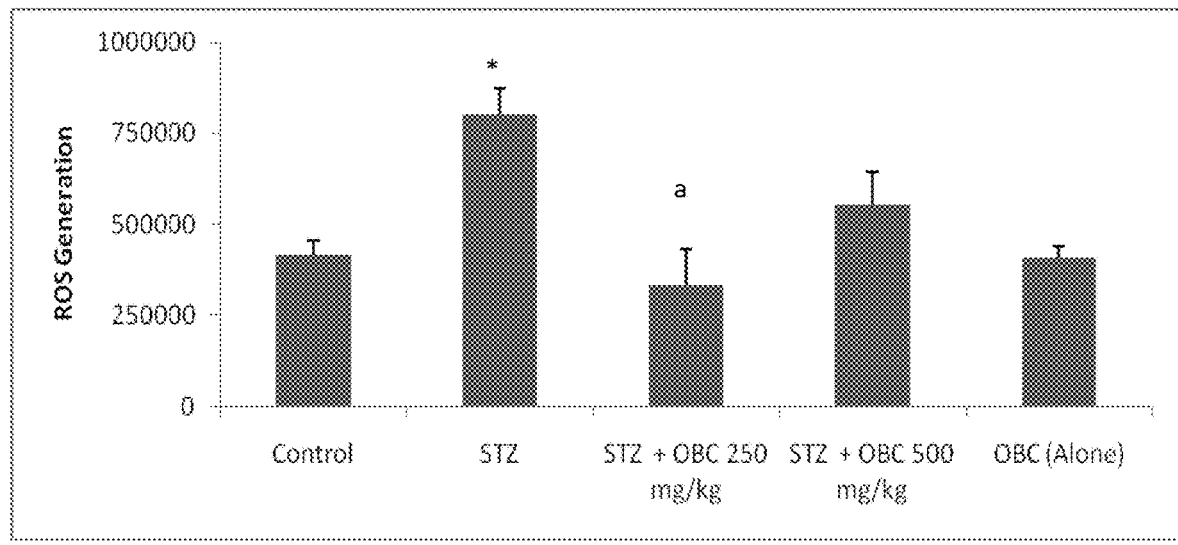
FIG. 10 is a graphical representation of the reduction in ROS levels in the cortex of streptozotocin treated animals administered with a composition containing oroxylin A, baicalein and chrysin.
Figure 11:
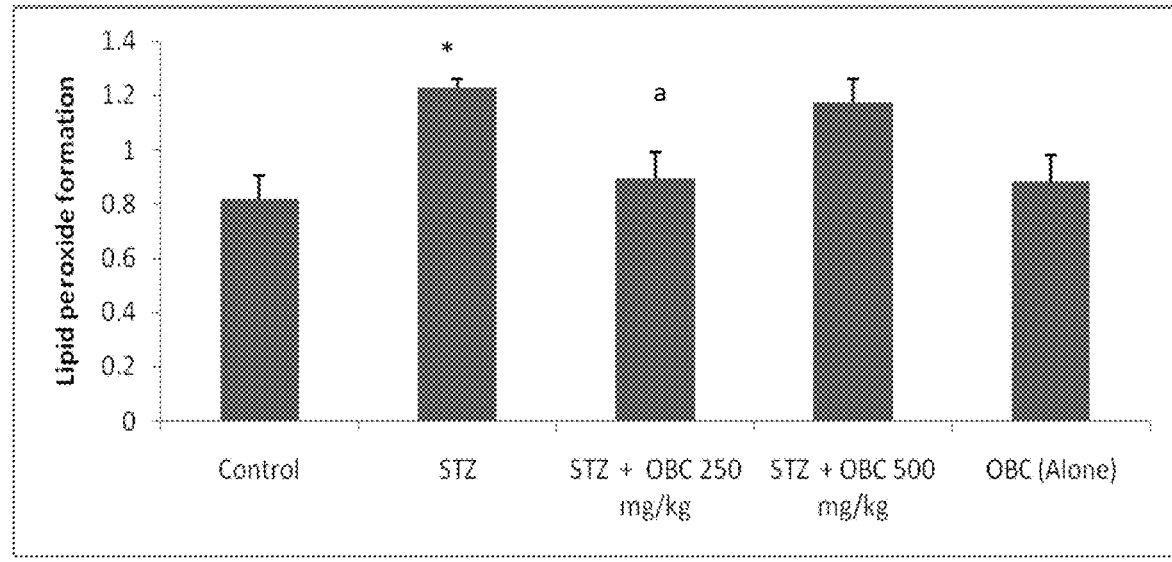
FIG. 11 is a graphical representation of the reduction in lipid peroxidation in the cortex of streptozotocin treated animals administered with a composition containing oroxylin A, baicalein and chlysin.
Figure 12:
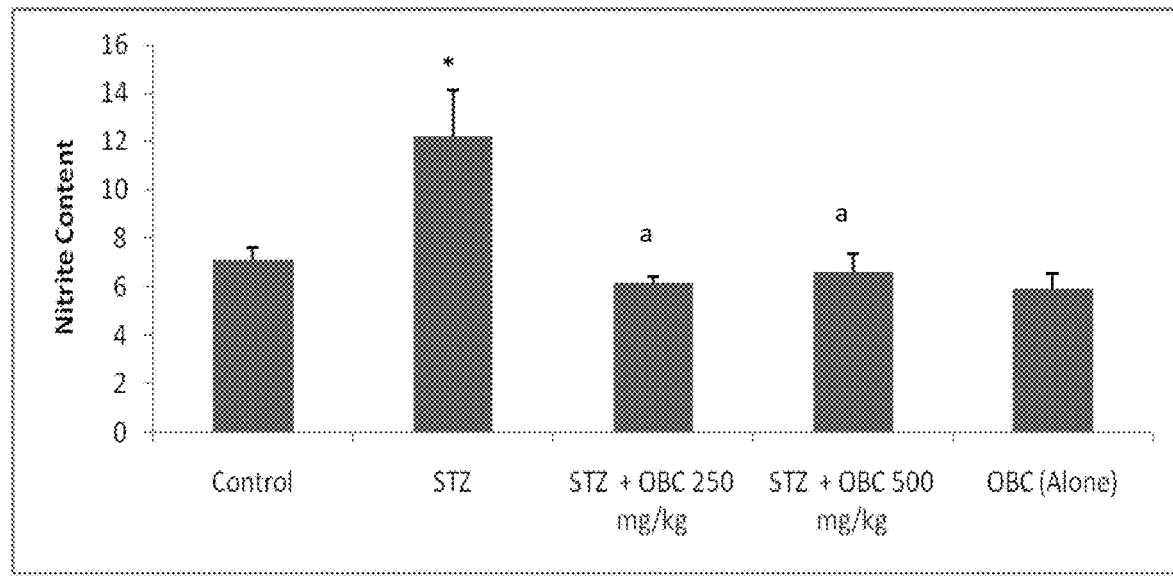
FIG. 12 is a graphical representation of the reduction in nitrate content in the cortex of streptozotocin treated animals administered with a composition containing oroxylin A, baicalein and chrysin.

STZ significantly increased the generation of ROS in the cortex as compared to the control (n=5, $*p<0.05$). The composition significantly lowered the ROS generated by STZ (n=5, $^a p<0.05$) (FIG. 10). Similarly, STZ significantly increased the lipid peroxidation in the cortex as compared to the control (n=5, $*p<0.05$). The composition at 250 mg/kg significantly lowered the lipid peroxide formed by STZ (n=5, $^a p<0.05$) (FIG. 11). With regard to the nitrite content, STZ significantly increased the nitrite in the cortex as compared to the control (n=5, $*p<0.05$). The composition at 250 mg/kg and 500 mg/kg significantly lowered the nitrite formed by STZ (n=5, $^a p<0.05$) (FIG. 12).

Enhancement of Mitochondrial Function

The role of mitochondria in memory impairment is well established. Reports indicated the decrease in activity of complex I and complex IV with aging (Swerdlow (2011) Brain aging, Alzheimer's disease, and mitochondria, Biochim Biophys Acta. 2011 December; 1812(12): 1630-1639). The activity of the complexes were also reported to be impaired in Alzheimer's induced memory dysfunction (Rhein et al., (2009) Amyloid-β and tau synergistically impair the oxidative phosphorylation system in triple transgenic Alzheimer's disease mice, Proc Natl Acad Sci USA 2009 Nov. 24; 106(47): 20057-20062). Hence, enhancement of the mitochondrial complex can be an important target in alleviating the symptoms of memory impairment.

Figure 13A:
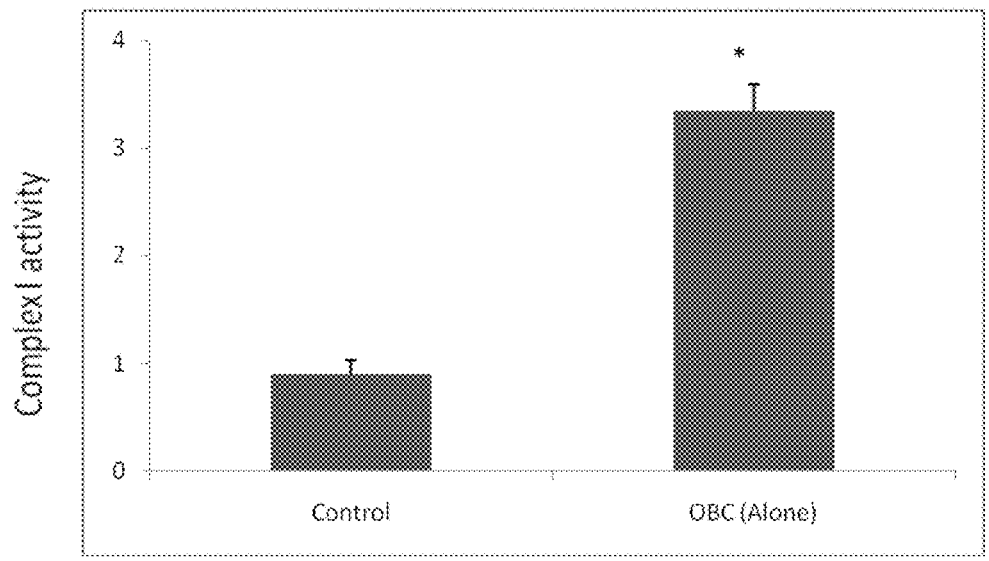
FIG. 13a is a graphical representation of the increase in complex I in the cortex of streptozotocin treated animals administered with a composition containing oroxylin A, baicalein and chrysin.
Figure 13B:
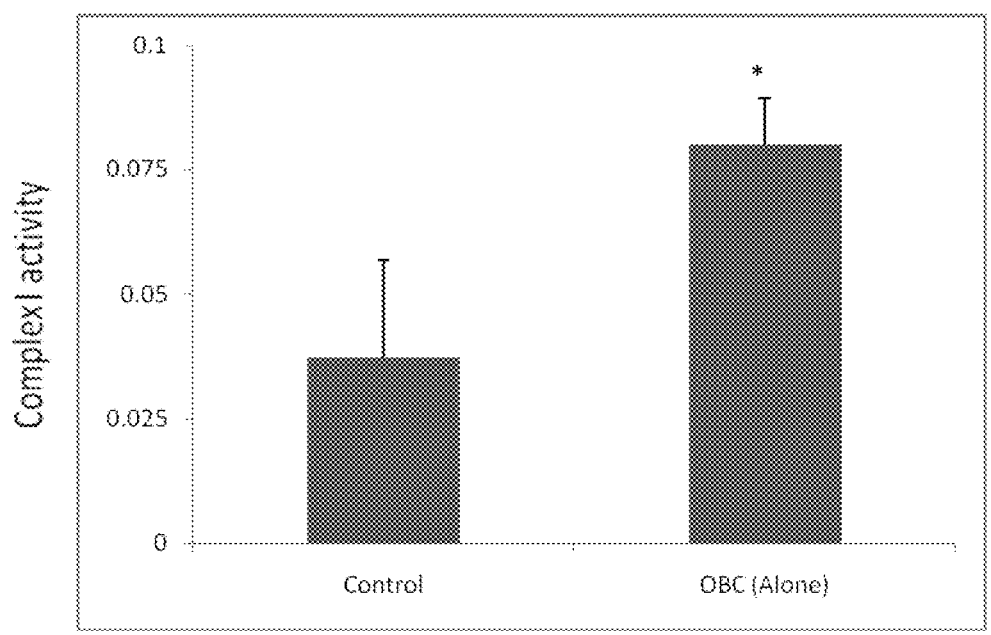
FIG. 13b is a graphical representation of the increase in complex I in brain (other than cortex) of streptozotocin treated animals administered with a composition containing oroxylin A, baicalein and chrysin.
Figure 14A:
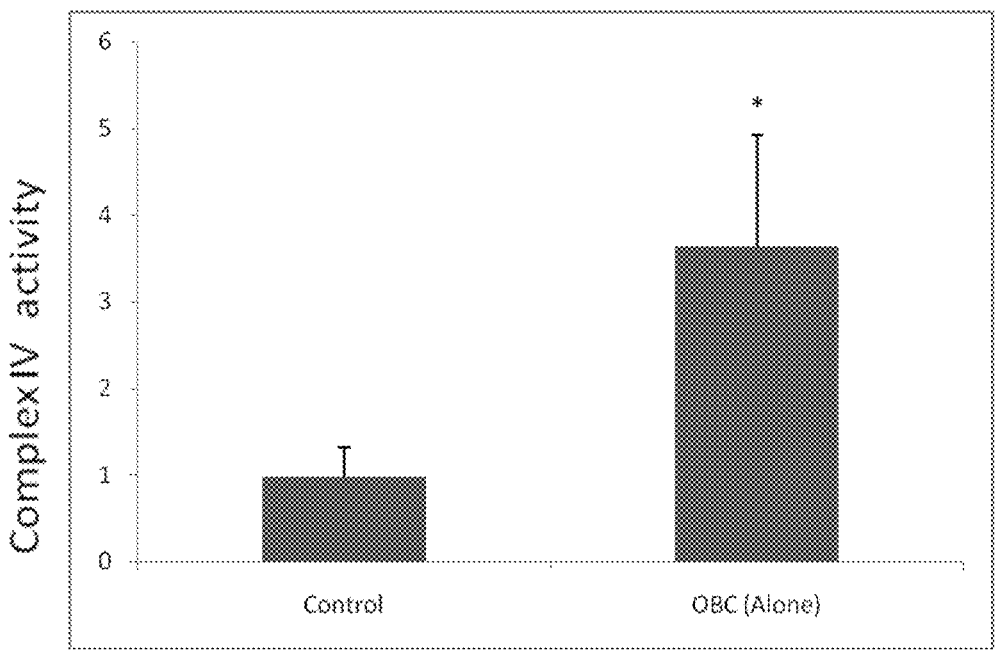
FIG. 14a is a graphical representation of the increase in complex IV in the cortex of streptozotocin treated animals administered with a composition containing oroxylin A, baicalein and chrysin.
Figure 14B:
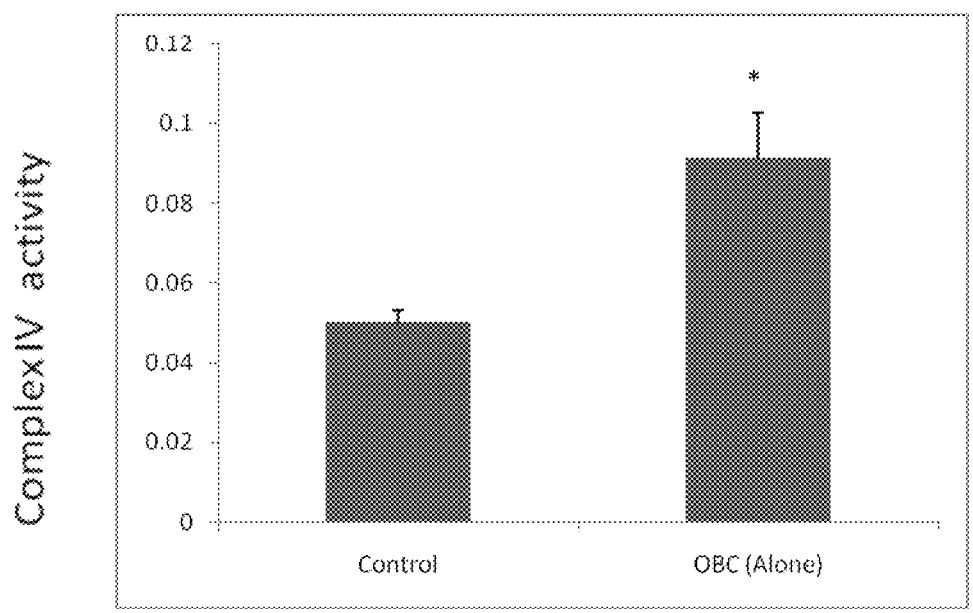
FIG. 14b is a graphical representation of the increase in complex IV in brain (other than cortex) of streptozotocin treated animals administered with a composition containing oroxylin A, baicalein and chrysin.

In the present study, the composition containing oroxylin A, baicalein and chrysin significantly increased the activity of complex I in both the cortex (FIG. 13a) and in the rest of the brain (FIG. 13b). Similarly, complex IV was also enhanced in the cortex (FIG. 14a) and in the rest of the brain (FIG. 14b) by the composition, compared to the control.

General Behavioral Markers:

The control and composition (500 mg/kg) treated rats were monitored regularly for several behavioral parameters mentioned below in table 2:

TABLE 2

Behavioral Parameters

| Behavioral Parameters | Control | OBC (500 mg/kg) |
|---|---|---|
| Abnormal posture (head press) | N | N |
| Aggressive behavior (fight) | N | N |
| Agitation | N | N |
| Allergic reaction (redness of the skin or eye) | N | N |
| Anaphylactic shock/death | N | N |
| Body Temperature (° C.) | 35.5 ± 0.02 | 35.51 ± 0.02 |
| Body weight | 367.2 ± 5.61 | 366 ± 3.8 |
| Bowel movement | N | N |
| Diarrhea | None | None |
| Drooling | N | N |
| Eye bulging | N | N |
| Fighting (Aggressive behavior) | N | N |
| Grinding teeth/Chattering | N | N |
| Grooming | Y | Y |
| Hair coat erection | N | N |
| Head twitching | N | N |
| Hematuria | N | N |
| Hind limb abduction | N | N |
| Hyperactivity (excessive jumping) | N | N |
| Licking body | N | N |
| Licking genitals | N | N |
| Mortality observed | N | N |
| Locomotion (increase/decrease) | N | N |
| Narcolepsy | N | N |
| Open mouth breathing | N | N |
| Penile erection (stimulatory behavior) | N | N |
| Rapid Breathing | N | N |
| Salivation/Drool | N | N |
| Seizure | N | N |
| Sniffing | N | N |
| Stool color | N | N |
| Straub tail | N | N |
| Sunken eyes/lack of blinking | N | N |
| Tremor | N | N |
| Tumor | N | N |
| Wiggling Whiskers | N | N |

Y = yes, N = no

Based on effect of body weight and temperature, the composition did not exhibit any major toxicity. The composition did not affect the growth and development of the rats as seen by the body weight. Furthermore, it also had no significant adverse effects pertaining to the Central Nervous System (CNS), Gastrointestinalsystem (GIT) and Genitourinary system.

Endocrinological Parameters Associated with Hyperglycemia:

In this study, we used streptozotocin (55 mg/kg) to induce hyperglycemia. We measured the levels of glucose using standardized glucometer after 4 weeks of treatment. Based on the literature, the current animal model represents severe hyperglycemia. Streptozotocin significantly elevated the levels of glucose as compared to the controls (445.5% increase, n=12, p<0.05). The composition (500 mg/kg) alone did not affect the blood glucose levels, however, the composition (250 and 500 mg/kg) did not reduce the hyperglycemia induced by Streptozotocin.

In conclusion, the composition containing oroxylin A, baicalein and chrysin was very effective in ameliorating the symptoms of chemotherapy and hyperglycemia induced memory impairment, indicating that it may be administered effectively to counter memory loss in disease like Alzheimer's disease, Vascular dementia, Parkinson's disease. Lewy body dementia, Fronto-temporal dementia, Creutzfeldt-Jakob disease, Wernicke's encephalopathy, Hydrocephalus, Huntington's disease, Vitamin B12 deficiency, thyroid dysfunction, anticholinergic medications induced dementia, chemotherapy induced cognitive dysfunction, hyperglycemia, and depression.

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A method of therapeutic management of neurotoxicity in mammals, said method comprising steps of administering effective concentration of a composition consisting essentially of 10%-15% w/w of oroxylin A, 10%-25% w/w of baicalein and 2%-10% w/w of chrysin, to mammals in need of such therapeutic management, wherein neurotoxicity is induced by chemotherapeutics; wherein the composition confers neuroprotection by improving cognition, decreasing oxidative stress, and enhancing mitochondrial function in the brain of mammals.

2. The method as in claim 1, wherein improvement in cognition is brought about by improving response time, orientation, recognition, short term working memory, spatial navigation and recall.

3. The method as in claim 1, wherein decrease in oxidative stress in brought about by decreasing the levels of reactive oxygen species (ROS), decreasing lipid peroxidation and increasing the glutathione content in the brain of mammals.

4. The method as in claim 1, wherein enhancement in mitochondrial function is brought about by increasing activity of complex I and complex IV in the mammalian brain.

5. The method as in claim 1, wherein the mammal is human.

6. The method as in claim 1, wherein the composition is formulated with pharmaceutically/nutraceutically acceptable excipients, adjuvants, diluents or carriers and administered orally in the form of tablets, capsules, syrups, gummies, powders, suspensions, emulsions, chewables, candies and eatables.

7. A method of therapeutic management of hyperglycemia induced neurotoxicity in mammals, said method comprising steps of administering effective concentration of a composition consisting essentially of 10%-15% w/w of oroxylin A, 10%-25% w/w of baicalein and 2%-10% w/w of chrysin, to mammals in need of such therapeutic management, wherein the composition confers neuroprotection by decreasing oxidative stress and enhancing mitochondrial function in the brain of mammals, thereby improving cognition.

8. The method as in claim 7, wherein decrease in oxidative stress in brought about by decreasing the levels of reactive oxygen species (ROS), decreasing lipid peroxidation and nitrate content in the brain of mammals.

9. The method as in claim 7, wherein enhancement in mitochondrial function is brought about by increasing activity of complex I and complex IV in the mammalian brain.

10. The method as in claim 7, wherein hyperglycemia is a pathological feature of diseases selected from diabetes, hypercholesterolemia, Alzheimer's disease, mild cognitive impairment, pancreatitis, carcinoma, and hyperthyroidism.

11. The method as in claim 7, wherein the mammal is human.

12. The method as in claim 7, wherein the composition is formulated with pharmaceutically/nutraceutically acceptable excipients, adjuvants, diluents or carriers and administered orally in the form of tablets, capsules, syrups, gummies, powders, suspensions, emulsions, chewables, candies and eatables.

* * * * *